(12) United States Patent
Sim et al.

(10) Patent No.: US 12,228,858 B2
(45) Date of Patent: Feb. 18, 2025

(54) COATING COMPOSITION FOR FORMING RESIST UNDERLAYER FILM FOR EUV LITHOGRAPHY PROCESS

(71) Applicant: ROHM AND HAAS ELECTRONIC MATERIALS KOREA LTD., Cheonan-si (KR)

(72) Inventors: Jae Hwan Sim, Cheonan-si (KR); Suwoong Kim, Cheonan-si (KR); Jin Hong Park, Cheonan-si (KR); Myung Yeol Kim, Cheonan-si (KR); Yoo-Jin Ghang, Cheonan-si (KR); Jae-Bong Lim, Cheonan-si (KR)

(73) Assignee: DUPONT SPECIALTY MATERIALS KOREA LTD, Chungcheongnam-Do (KR)

( * ) Notice: Subject to any disclaimer, the term of this patent is extended or adjusted under 35 U.S.C. 154(b) by 577 days.

(21) Appl. No.: 16/176,245

(22) Filed: Oct. 31, 2018

(65) Prior Publication Data

US 2020/0133126 A1 Apr. 30, 2020

(51) Int. Cl.
| | | |
|---|---|---|
| *G03F 7/09* | (2006.01) | |
| *C07D 251/32* | (2006.01) | |
| *C08F 224/00* | (2006.01) | |
| *C08G 71/00* | (2006.01) | |
| *C08G 73/06* | (2006.01) | |
| *G03F 7/004* | (2006.01) | |
| *G03F 7/11* | (2006.01) | |
| *G03F 7/16* | (2006.01) | |
| *G03F 7/20* | (2006.01) | |
| *G03F 7/30* | (2006.01) | |
| *G03F 7/32* | (2006.01) | |
| *G03F 7/38* | (2006.01) | |

(52) U.S. Cl.
CPC .............. *G03F 7/11* (2013.01); *C07D 251/32* (2013.01); *C08G 71/00* (2013.01); *G03F 7/0045* (2013.01); *G03F 7/091* (2013.01); *G03F 7/092* (2013.01); *G03F 7/162* (2013.01); *G03F 7/168* (2013.01); *G03F 7/2004* (2013.01); *G03F 7/2037* (2013.01); *G03F 7/30* (2013.01); *G03F 7/322* (2013.01); *G03F 7/38* (2013.01)

(58) Field of Classification Search
CPC ......... G03F 7/091; G03F 7/092; C08G 73/06; C08G 73/0644; C08F 224/00
See application file for complete search history.

(56) References Cited

U.S. PATENT DOCUMENTS

| | | | |
|---|---|---|---|
| 6,852,421 B2 | 2/2005 | Wayton et al. | |
| 9,214,345 B2 * | 12/2015 | Ohashi | ................. C09D 201/02 |
| 9,250,525 B2 | 2/2016 | Endo et al. | |
| 9,910,364 B2 | 3/2018 | Sakaida et al. | |
| 9,927,705 B2 | 3/2018 | Fujitani et al. | |
| 2006/0057491 A1 | 3/2006 | Wayton et al. | |
| 2010/0230136 A1* | 9/2010 | Ichikawa | ............ H01L 21/0274 |
| | | | 174/250 |
| 2010/0297542 A1* | 11/2010 | Hayoz | ...................... C09D 4/00 |
| | | | 430/7 |
| 2011/0033801 A1 | 2/2011 | Zampini et al. | |
| 2011/0230058 A1* | 9/2011 | Sakamoto | ............... G03F 7/093 |
| | | | 438/763 |
| 2015/0185614 A1 | 7/2015 | Sim et al. | |

FOREIGN PATENT DOCUMENTS

| | | |
|---|---|---|
| CN | 107501858 A | 12/2017 |
| JP | 2013203825 A1 | 10/2013 |
| KR | 20110095362 A | 8/2011 |
| KR | 20120022889 A | 3/2012 |
| KR | 20120045028 A | 5/2012 |
| KR | 101682919 B1 | 12/2016 |

* cited by examiner

*Primary Examiner* — John S. Chu
(74) *Attorney, Agent, or Firm* — CANTOR COLBURN LLP

(57) ABSTRACT

A monomer represented by Chemical Formula (1):

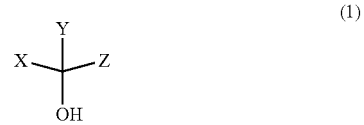

wherein, X, Y, and Z are the same as described in the specification, and the polymer including repeat units derived from the monomer.

11 Claims, No Drawings

COATING COMPOSITION FOR FORMING RESIST UNDERLAYER FILM FOR EUV LITHOGRAPHY PROCESS

FIELD

The present disclosure generally relates to underlayer coating compositions for use with photoresist compositions. Specifically, the disclosure provides coating compositions for forming resist underlayer film for extreme ultraviolet ("EUV") lithography.

BACKGROUND

EUV lithography is one of the leading technology options to replace optical lithography for volume semiconductor manufacturing at feature sizes of several nanometers. Currently, EUV lithography has become the preferred patterning technology over 193 nm immersion processes for high volume manufacturing for product nodes under 10 nm.

It is well-known that the number of photon at the exposed area in EUV lithography is much smaller than that in ArF lithography. Due to the lack of photon and shrunken pitches of patterns, impact of shot noise becomes more significant on pattern profiles. As a result, new issues that have not been observed in ArF lithography, arise in the recent EUV lithography techniques. As the most serious issue, a nano-bridging defect at line to space patterns with 3× nm pitches has been reported. It can cause fatal bridging defect after whole pattern transfer by etching process.

It has been found that the nano-bridging defect results from an intrinsic lack of acid at the bottom of a photo-resist by EUV patterning mechanism. A chemical approach is therefore required to mitigate this kind of defect. There remains a need in new materials capable of mitigating the nano-bridging defect in photoresists.

SUMMARY

It has been found that certain underlayer compositions providing additional acid to the interface between the newly designed polymer structure and the photoacid generator having high EUV absorption improve photo-speed and scum/footing profile of the EUV photoresist. The compositions described in the present application significantly reduce nano-bridging defect compared to the photoresist on a CVD hardmask stack.

An embodiment provides a monomer represented by Chemical Formula (1):

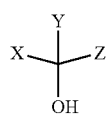

(1)

wherein,
X is a linear or branched C1 to C10 hydrocarbon group, a C1 to C10 alkoxycarbonyl group, a C1 to C10 alkanoyloxy group, a carboxylic acid group, or a linear or branched C1 to C10 hydroxyalkyl group optionally substituted with a C1 to C5 alkoxycarbonyl group or a C1 to C5 substituted alkoxy group;
Y is a hydrogen, a linear or branched C1 to C10 hydrocarbon group, a C1 to C10 alkoxycarbonyl group, or a C1 to C10 alkanoyloxy group, a carboxylic acid group, or a linear or branched C1 to C10 hydroxyalkyl group optionally substituted with a C1 to C5 alkoxycarbonyl group or a C1 to C5 alkoxy group; and
Z is a linear or branched C1 to C10 hydrocarbon group, a C1 to C10 alkoxycarbonyl group, a C1 to C10 alkanoyloxy group, a carboxylic acid group, or a linear or branched C1 to C10 hydroxyalkyl group optionally substituted with a C1 to C5 alkoxycarbonyl group or a C1 to C5 alkoxy group,
wherein each of the C1 to C10 hydrocarbon group, the C1 to C10 alkoxycarbonyl group, the C1 to C10 alkanoyloxy group, and the C1 to C10 hydroxyalkyl group is optionally substituted with at least one selected from the group consisting of fluorine, chlorine, bromine, iodine, a hydroxyl group, a thiol group, a carboxylic acid group, a C1 to C5 alkyl group, a C3 to C8 cycloalkyl group, a C2 to C5 alkenyl group, a C1 to C5 alkoxy group, a C2 to C5 alkenoxy group, a C6 to C10 aryl group, a C6 to C10 aryloxy group, a C7 to C10 alkylaryl group, and a C7 to C10 alkylaryloxy group.

Another embodiment provides a polymer including repeat units derived from the monomer.

Still another embodiment provides an underlayer coating composition including a polymer, a crosslinking agent, and a solvent. The composition may further include a photoacid generator.

Yet another embodiment provides a method of forming an electronic device, comprising:
(a) applying a layer of the underlayer coating composition on a substrate;
(b) curing the underlayer coating composition to form an underlayer film;
(c) applying a layer of a photoresist composition on the underlayer film to form a photoresist layer;
(d) pattern-wise exposing the photoresist layer to radiation; and
(e) developing the exposed photoresist layer to provide a resist relief image.

DETAILED DESCRIPTION

Reference will now be made in detail to exemplary embodiments, examples of which are illustrated in the present description. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, when a definition is not otherwise provided, the term "hydrocarbon group" refers to an organic compound having at least one carbon atom and at least one hydrogen atom, optionally substituted with one or more substituents where indicated.

As used herein, when a definition is not otherwise provided, the term "alkyl group" refers to a group derived from a straight or branched chain saturated aliphatic hydrocarbon having the specified number of carbon atoms and having a valence of at least one.

As used herein, when a definition is not otherwise provided, the term "hydroxyalkyl group" refers to an alkyl group substituted with at least one hydroxyl group (—OH).

As used herein, when a definition is not otherwise provided, the term "alkoxy group" refers to "alkyl-O—", wherein the term "alkyl" has the same meaning as "alkyl group" described above.

As used herein, when a definition is not otherwise provided, the term "alkanoyloxy group" refers to a group having the formula "alkyl-C(=O)—O—", wherein "alkyl" has the same meaning as "alkyl group" described above.

As used herein, when a definition is not otherwise provided, the term "alkoxycarbonyl group" refers to a group having the formula "alkyl-O—C(=O)—", wherein "alkyl" has the same meaning as "alkyl group" described above.

As used herein, when a definition is not otherwise provided, the term "carboxylic acid group" refers to a group having the formula "—C(=O)—OH".

As used herein, when a definition is not otherwise provided, the term "cycloalkyl group" refers to a monovalent group having one or more saturated rings in which all ring members are carbon.

As used herein, when a definition is not otherwise provided, the term "alkenyl group" refers to a straight or branched chain, monovalent hydrocarbon group having at least one carbon-carbon double bond.

As used herein, when a definition is not otherwise provided, the term "alkenoxy group" refers to "alkenyl-O—", wherein the term "alkenyl" has the same meaning as "alkenyl group" described above.

As used herein, when a definition is not otherwise provided, the term "aryl group", which is used alone or in combination, refers to an aromatic or heteroaromatic hydrocarbon containing at least one ring and having the specified number of carbon atoms. The term "aryl group" may be construed as including a group with an aromatic or heteroaromatic ring fused to at least one cycloalkyl or heterocycloalkyl ring. The "aryl" group may include one or more heteroatom(s) independently selected from nitrogen (N), oxygen (O), P (phosphorus), and sulfur (S).

As used herein, when a definition is not otherwise provided, the term "aryloxy group" refers to "aryl-O—", wherein the term "aryl" has the same meaning as "aryl group" described above.

As used herein, when a definition is not otherwise provided, the term "alkylaryl group" refers to an alkyl group covalently linked to a substituted or unsubstituted aryl group that is linked to a compound.

As used herein, when a definition is not otherwise provided, the term "alkylaryloxy group" refers to "alkylaryl-O—", wherein the term "alkylaryl" has the same meaning as "alkylaryl group" described above.

Monomer

In an embodiment, a monomer represented by Chemical Formula (1) is provided:

(1)

In Chemical Formula (1), X may be a linear or branched C1 to C10 hydrocarbon group, a C1 to C10 alkoxycarbonyl group, a C1 to C10 alkanoyloxy group, a carboxylic acid group, or a linear or branched C1 to C10 hydroxyalkyl group, which may be substituted with a C1 to C5 alkoxycarbonyl group or a C1 to C5 substituted alkoxy group.

In Chemical Formula (1), Y may be a hydrogen, a linear or branched C1 to C10 hydrocarbon group, a C1 to C10 alkoxycarbonyl group, a C1 to C10 alkanoyloxy group, a carboxylic acid group, or a linear or branched C1 to C10 hydroxyalkyl group, which may be substituted with a C1 to C5 alkoxycarbonyl group or a C1 to C5 alkoxy group.

In Chemical Formula (1), Z may be a linear or branched C1 to C10 hydrocarbon group, a C1 to C10 alkoxycarbonyl group, a C1 to C10 alkanoyloxy group, a carboxylic acid group, or a linear or branched C1 to C10 hydroxyalkyl group, which may be substituted with a C1 to C5 alkoxycarbonyl group or a C1 to C5 alkoxy group.

Groups X, Y, and Z may further include a substituent. In some embodiments, each of the C1 to C10 hydrocarbon group, the C1 to C10 alkoxycarbonyl group, the C1 to C10 alkanoyloxy group, and the C1 to C10 hydroxyalkyl group constituting X, Y, and Z in Chemical Formula (1) may be substituted with at least one selected from the group consisting of fluorine, chlorine, bromine, iodine, a hydroxyl group, a C1 to C5 alkyl group, a C3 to C8 cycloalkyl group, a C2 to C5 alkenyl group, a C1 to C5 alkoxy group, a C2 to C5 alkenoxy group, a C6 to C10 aryl group, a C6 to C10 aryloxy group, a C7 to C10 alkylaryl group, and a C7 to C10 alkylaryloxy group.

In some embodiments, a substituent may be a hydroxyl group. That is each of X, Y, and Z may include 1, 2, 3, 4, or 5 hydroxyl groups. In other embodiment, a substituent may be a carboxylic acid group. That is each of X, Y, and Z may include 1, 2, 3, 4, or 5 carboxylic acid groups.

When Y is hydrogen, the monomer represented by Chemical Formula (1) may be a secondary alcohol. When Y is a group other than hydrogen, the monomer represented by Chemical Formula (1) may be a tertiary alcohol.

Non-limiting examples of the monomer represented by Chemical Formula (1) include the following compounds:

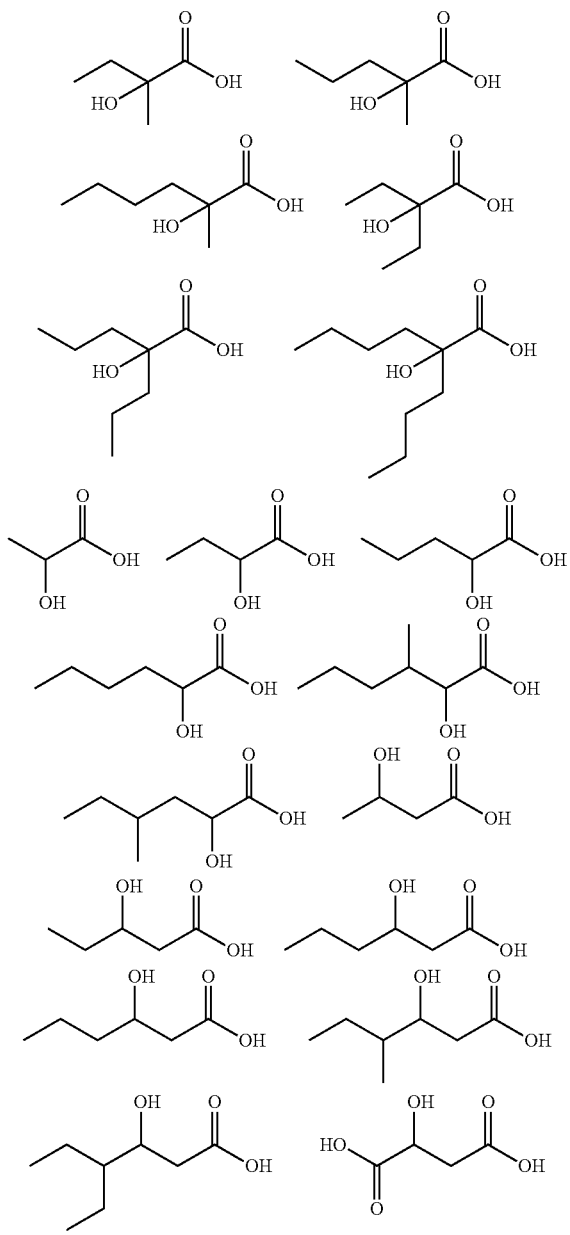

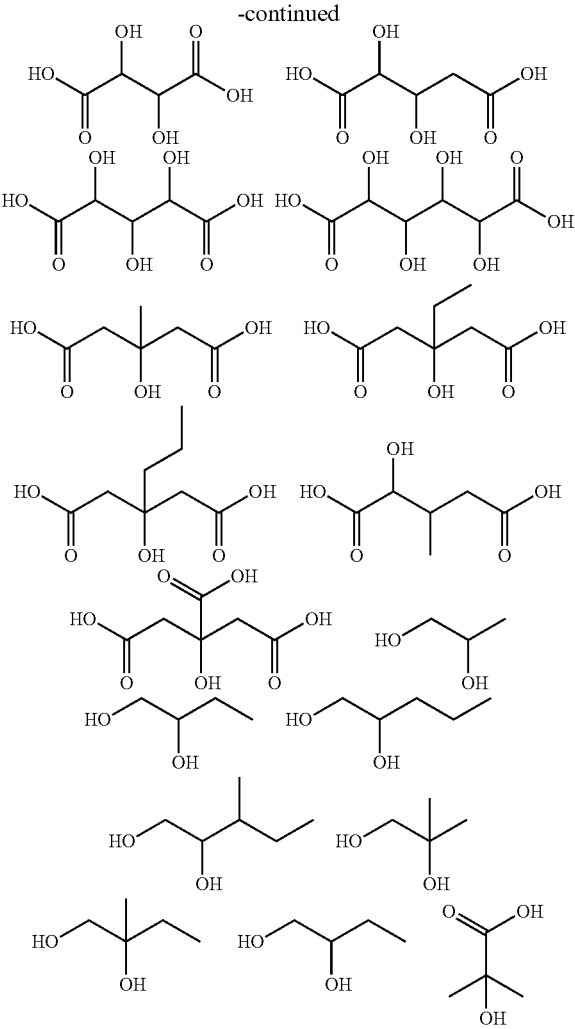

Polymer

In another embodiment, a polymer including repeat units derived from the above monomer is provided. The features of the polymer may be understood by referring to the described above features of the monomer. In the polymer, at least one selected from X, Y, and Z may include a carboxylic acid group.

The amount of the repeat units derived from the monomer represented by Chemical Formula (1) may be 5-30 mol %, for example, 10-20 mol %, based on the total number of the repeat units in the polymer.

The polymer may further include repeat units derived from a monomer represented by Chemical Formula (2):

(2)

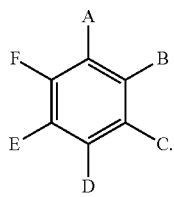

Non-limiting examples of the monomer represented by Chemical Formula (2) include the following compounds:

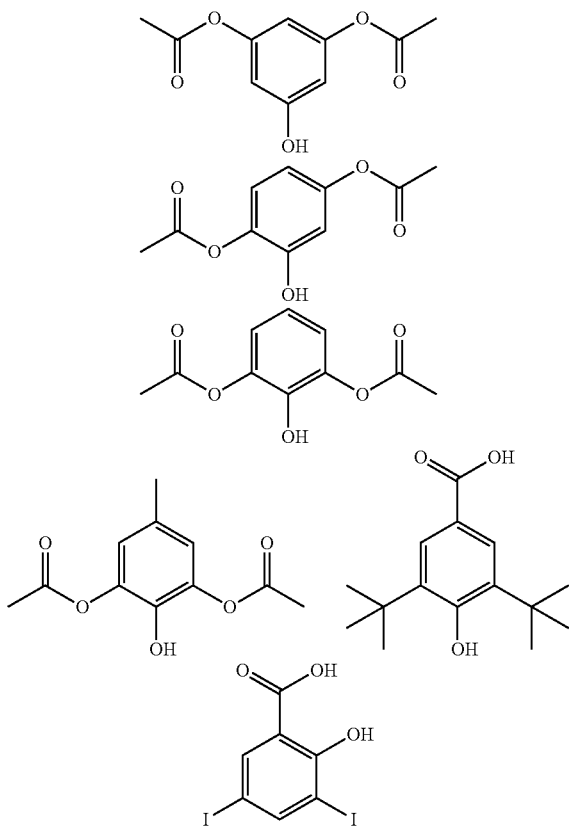

The amount of the repeat units derived from the monomer represented by Chemical Formula (2) may be 10-40 mol %, for example, 15-30 mol %, based on the total number of the repeat units in the polymer.

In Chemical Formula (2), A, B, C, D, E, and F may each independently be a hydrogen, a halogen, a hydroxyl group, a carboxylic acid group, a C1 to C10 alkoxycarbonyl group, a C1 to C10 alkoxy group, a linear or branched C1 to C10 hydrocarbon group, a C1 to C10 alkoxycarbonyl group, or a C1 to C10 alkanoyloxy group.

Each of the C1 to C10 alkoxycarbonyl group, the C1 to C10 alkoxy group, the C1 to C10 hydrocarbon group, the C1 to C10 alkoxycarbonyl group, and the C1 to C10 alkanoyloxy group constituting A, B, C, D, E, and F may be substituted with at least one selected from the group consisting of fluorine, chlorine, bromine, iodine, C1 to C5 alkyl, C3 to C8 cycloalkyl, C2 to C5 alkenyl, C1 to C5 alkoxy, C2 to C5 alkenoxy, C6 to C10 aryl, C6 to C10 aryloxy, C7 to C10 alkylaryl, and C7 to C10 alkylaryloxy.

In Chemical Formula (2), at least one selected from A, B, C, D, E, and F may include a hydroxyl group. The number of the hydroxyl groups may be 1, 2, 3, 4, or 5, but is not limited thereto.

In Chemical Formula (2), at least one selected from A, B, C, D, E, and F may include one or more iodine atoms. The number of the iodine atoms may be 1, 2, 3, 4, or 5, but is not limited thereto.

In Chemical Formula (2), at least one selected from A, B, C, D, E, and F may include one or more carboxylic acid groups. The number of the carboxylic acid groups may be 1, 2, 3, 4, or 5, but is not limited thereto.

The polymer may further include repeat units derived from a monomer represented by Chemical Formula (3):

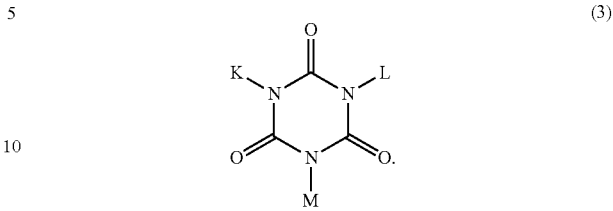

(3)

In Chemical Formula (3), K, L, and M may each independently be a linear or branched C1 to C10 hydrocarbon group, a C1 to C10 alkoxycarbonyl group, a C1 to C10 alkanoyloxy group, wherein each of these groups may be substituted with a carboxylic acid group. K, L, and M may each independently be a linear or branched C1 to C10 hydroxyalkyl group, which may be substituted with a C1 to C5 alkoxycarbonyl group or a C1 to C5 substituted alkoxy group. At least one selected from K, L, and M may include a halogen atom selected from the group consisting of fluorine, chlorine, bromine, and iodine, a hydroxyl group, a carboxylic group, or a combination thereof.

In Chemical Formula (3), K, L, and M may be each independently a linear or branched C1 to C10 hydrocarbon group, a C1 to C10 alkoxycarbonyl group, a C1 to C10 alkanoyloxy group, each of which may be optionally substituted with a carboxylic acid group, or a linear or branched C1 to C10 hydroxyalkyl group optionally substituted with a C1 to C5 alkoxycarbonyl group or a C1 to C5 substituted alkoxy group, wherein each of the C1 to C10 hydrocarbon group, the C1 to C10 alkoxycarbonyl group, the C1 to C10 alkanoyloxy group, and the C1 to C10 hydroxyalkyl group may be optionally substituted with at least one selected from the group consisting of fluorine, chlorine, bromine, iodine, C1 to C5 alkyl, C3 to C8 cycloalkyl, C2 to C5 alkenyl, C1 to C5 alkoxy, C2 to C5 alkenoxy, C6 to C10 aryl, C6 to C10 aryloxy, C7 to C10 alkylaryl, and C7 to C10 alkylaryloxy.

In Chemical Formula (3), at least one selected from K, L, and M may include one or more halogen atoms. The number of the halogen atoms may be 1, 2, 3, 4, or 5, but is not limited thereto.

In Chemical Formula (3), at least one selected from K, L, and M may include a hydroxyalkyl group. The number of the hydroxyl groups in the compound may be 1, 2, 3, 4, or 5, but is not limited thereto.

In Chemical Formula (3), at least one selected from K, L, and M may include one or more carboxylic acid groups. The number of the carboxylic acid groups may be 1, 2, 3, 4, or 5, but is not limited thereto.

The amount of the repeat units derived from the monomer represented by Chemical Formula (3) may be 10 to 60 mol %, for example, 30 to 50 mol %, based on the total number of the repeat units in the polymer.

Underlayer Coating Composition and Film

Another embodiment provides an underlayer coating composition including a polymer, a crosslinking agent, and a solvent.

The underlayer coating composition may be a crosslinked organic film, which may have a substantially reduced thickness. In some embodiments, the underlayer coating composition film layer dried thickness may be about 200 Å or less, of about 150 Å or less, of about 100 Å or less of about 90 Å or less, of about 80 Å or less, of about 70 Å or less, of about 60 Å or less, or of about 50 Å or less. In an exemplary embodiment, the applied underlayer coating composition may suitably have a thickness of 50 Å or less.

The applying methods of the underlayer coating composition above the substrate are not particularly limited among the method generally used in the related arts. Exemplary methods may include, but are not limited to, dipping, spraying, or spin coating. For example, the underlayer coating composition may be spin coated on the substrate. In addition, the coating composition may be spin coated on the substrate and thermally treated to provide a coating composition layer that is at least substantially free of pinholes.

In some embodiments, the underlayer coating composition layer may suitably be thermally treated to remove solvent and provide a thermally treated coating composition layer having a thickness of 100 Å or less, or 60 or 50 Å or less. Thermal treating may be performed at a variety of conditions such as at a temperature of about 160° C. or greater, or about 180° C. or greater, or about 200° C. or greater for 30 to 90 seconds.

The solvent component of an underlayer coating composition may be a single solvent or may include a mixture of two or more distinct solvents. Suitably, each of the multiple solvents may be miscible with each other.

The polymer component of the underlayer coating composition may have a weight average molecular weight (Mw) of about 1,000 to about 10,000,000 Daltons, for example, about 2,000 to about 10,000 Daltons, and a number average molecular weight (Mn) of about 500 to about 1,000,000 Daltons, for example, about 2,000 to about 10,000 Daltons. Molecular weights (either Mw or Mn) of the polymer of the composition may be suitably determined by gel permeation chromatography.

The polymer component may be the major solid component of the underlayer coating composition in a variety of embodiments. For instance, the polymer may suitably be present in an amount from 50 to 99.9 weight percent based on total solid content of the coating composition, for example, from 80 or 85 to 95 weight percent, 98 weight percent, greater than 99 (or even 100) weight percent based on total solid content of a coating composition. As used herein, the "solid content" of a coating composition refers to all materials of the coating composition except the solvent carrier.

Suitable polymers and polymer films for use in the present underlayer coating compositions can be readily prepared based on and by analogy with the procedures described in the examples of the present application, which are readily understood by those of ordinary skill in the art.

As discussed above, in certain embodiments, the coating composition may include a crosslinker in addition to or as a component of a resin. For example, the coating composition may include amine-based crosslinkers such as melamine materials, including melamine resins such as manufactured by Cytec Industries and sold under the tradename of Cymel 300, 301, 303, 350, 370, 380, 1116 and 1130; glycolurils including those glycolurils available from Cytec Industries; and benzoquanamines and urea-based materials including resins such as the benzoquanamine resins available from Cytec Industries under the name Cymel 1123 and 1125, and urea resins available from Cytec Industries under the names of Powderlink 1174 and 1196. In addition to being commercially available, such amine-based crosslinkers may be prepared, for example, by the reaction of acrylamide or methacrylamide copolymers with formaldehyde in an alcohol-containing solution, or alternatively by the copolymerization of N-alkoxymethyl acrylamide or methacrylamide with other suitable monomers.

Underlayer coating compositions may also contain additional dye compounds that absorb radiation used to expose an overcoated photoresist layer.

Underlayer coating compositions may further contain other materials such as one or more acid generator compounds, including one or more thermal acid generators and/or photoacid generators. Suitable photoacid generator for use in an underlayer coating composition include photoacid generators disclosed herein for an overcoated photoresist composition. See U.S. Pat. No. 6,261,743 for a discussion of such use of a photoacid generator in an underlying coating composition.

To make a liquid underlayer coating composition, the components of the coating composition may be dissolved in a suitable solvent such as, for example, one or more oxy-isobutyric acid esters particularly methyl-2-hydroxyisobutyrate, ethyl lactate or one or more of the glycol ethers such as 2-methoxyethyl ether (diglyme), ethylene glycol monomethyl ether, and propylene glycol monomethyl ether; solvents that have both ether and hydroxy moieties such as methoxy butanol, ethoxy butanol, methoxy propanol, and ethoxy propanol; methyl 2-hydroxyisobutyrate; esters such as methyl cellosolve acetate, ethyl cellosolve acetate, propylene glycol monomethyl ether acetate, dipropylene glycol monomethyl ether acetate and other solvents such as dibasic esters, propylene carbonate and gamma-butyrolactone.

As discussed, the solvent component may contain one or more solvents having a boiling of 200° C. or greater. In some embodiments, solvents having a boiling point of great than 200° C. include gamma butyrolactone, N-methyl pyrrolidine, and benzyl benzoate.

As also discussed, provided are underlayer coating compositions including at least 0.5 or 1 of the total weight percent of all solvent present in the coating composition is one or more solvents having a boiling point of 200° C. or greater such as one or more of gamma butyrolactone; N-methyl pyrrolidine; and/or benzyl benzoate. In certain aspects, an underlayer coating composition will contain no more than 70, 60, 50, 40, 30, 20, or 10 of solvent(s) having a boiling point of 200° C. or greater (such as gamma butyrolactone; N-methyl pyrrolidine; and/or benzyl benzoate) based on total weight of solvent present in the coating compositions.

The concentration of the dry components in the solvent will depend on several factors such as the method of application. In general, the solid content of an underlayer coating composition varies from about 0.1 to 20 weight percent of the total weight of the coating composition, preferably the solid content varies from about 0.1 to 10 weight of the coating composition.

The underlayer coating composition may be formulated with one or more photoacid generator. Suitable photoacid generator for use in an underlayer coating composition include photoacid generators disclosed herein for an overcoated photoresist composition. See U.S. Pat. No. 6,261,743 for a discussion of such use of a photoacid generator in an underlying coating composition. For example, the photoacid generator may be a small molecule compound having Chemical Formula (IV):

$$G^+Z^-$$ Chemical Formula (IV)

wherein G has Chemical Formula (V):

Chemical Formula (V)

In Chemical Formula (V), X may be S or I. Each $R^0$ is attached to X and may independently be a $C_{1-30}$ alkyl group; a polycyclic or monocyclic $C_{3-30}$ cycloalkyl group; a polycyclic or monocyclic $C_{6-30}$ aryl group; or a combination comprising at least one of the foregoing. r5 may be 2 or 3, provided that when X is I, r5 is 2, and when X is S, r5 is 2 or 3. In Chemical Formula (IV), Z may include the anion of a sulfonic acid, a sulfonimide, or a sulfonamide.

For example, cation $G^+$ may have Chemical Formulae (VI), (VII), or (VIII):

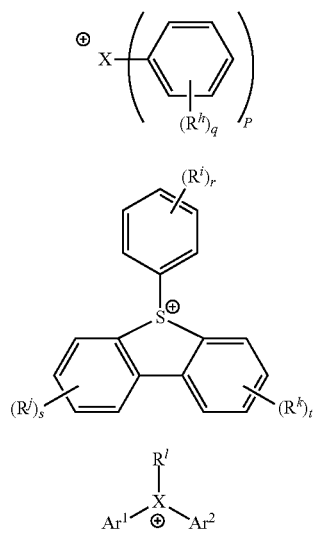

wherein
X is I or S,
$R^h$, $R^i$, $R^j$, and $R^k$ are unsubstituted or substituted and are each independently hydroxy, nitrile, halogen, $C_{1-30}$ alkyl, $C_{1-30}$ fluoroalkyl, $C_{3-30}$ cycloalkyl, $C_{1-30}$ fluorocycloalkyl, $C_{1-30}$ alkoxy, $C_{3-30}$ alkoxycarbonylalkyl, $C_{3-30}$ alkoxycarbonylalkoxy, $C_{3-30}$ cycloalkoxy, $C_{5-30}$ cycloalkoxycarbonylalkyl, $C_{5-30}$ cycloalkoxycarbonylalkoxy, $C_{1-30}$ fluoroalkoxy, $C_{3-30}$ fluoroalkoxycarbonylalkyl, $C_{3-30}$ fluoroalkoxycarbonylalkoxy, $C_{3-30}$ fluorocycloalkoxy, $C_{5-30}$ fluorocycloalkoxycarbonylalkyl, $C_{5-30}$ fluorocycloalkoxycarbonylalkoxy, $C_{6-30}$ aryl, $C_{6-30}$ fluoroaryl, $C_{6-30}$ aryloxy, or $C_{6-30}$ fluoroaryloxy, each of which is unsubstituted or substituted;
$Ar^1$ and $Ar^2$ are independently $C_{10-30}$ fused or singly bonded polycyclic aryl groups;
$R^l$ is a lone pair of electrons where X is I, or a $C_{6-20}$ aryl group where X is S;
p is an integer of 2 or 3, wherein when X is I, p is 2, and where X is S, p is 3,
q and r are each independently an integer from 0 to 5, and s and t are each independently an integer from 0 to 4.

In Chemical Formulae (VI), (VII), and (VIII), at least one of $R^h$, $R^i$, $R^j$, and $R^k$ may be an acid-cleavable group. In an embodiment, the acid-cleavable group may be (i) a tertiary $C_{1-30}$ alkoxy (for example, a tert-butoxy group), a tertiary $C_{3-30}$ cycloalkoxy group, a tertiary $C_{1-30}$ fluoroalkoxy group, (ii) a tertiary $C_{3-30}$ alkoxycarbonylalkyl group, a tertiary $C_{5-30}$ cycloalkoxycarbonylalkyl group, a tertiary $C_{3-30}$ fluoroalkoxycarbonylalkyl group, (iii) a tertiary $C_{3-30}$ alkoxycarbonylalkoxy group, a tertiary $C_{5-30}$ cycloalkoxycarbonylalkoxy group, a tertiary $C_{3-30}$ fluoroalkoxycarbonylalkoxy group, or (iv) a $C_{2-30}$ acetal group including moiety —O—C($R^{11}R^{12}$)—O— (wherein $R^{11}R^{12}$ are each independently hydrogen or a $C_{1-30}$ alkyl group).

Non-limiting examples of the photoacid generator include the following compounds:

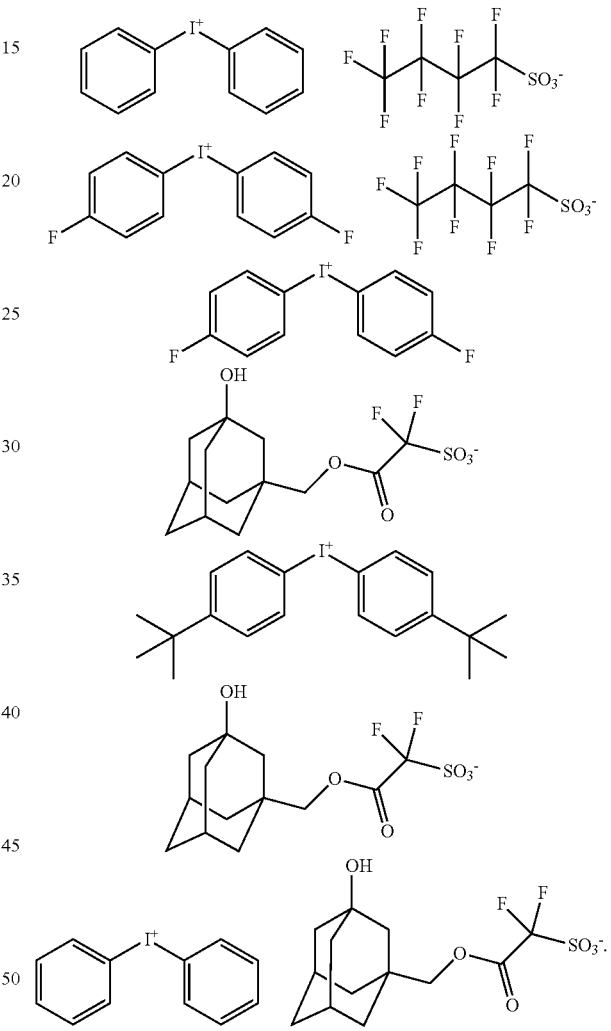

The amount of the photoacid generator may be 1-15 weight %, for example, 4-10 weight %, based on the total weight of the composition.

Other components of the photoresist may include solvents and surfactants.

Solvents generally suitable for dissolving, dispensing, and coating the components may include anisole, alcohols including ethyl lactate, methyl 2-hydroxybutyrate (HBM), 1-methoxy-2-propanol (also referred to as propylene glycol methyl ether, PGME), and 1-ethoxy-2 propanol, esters including n-butylacetate, 1-methoxy-2-propyl acetate (also referred to as propylene glycol methyl ether acetate, PGMEA), methoxyethoxypropionate, ethoxyethoxypropionate, and gamma-butyrolactone, ketones including cyclohexanone and 2-heptanone, and a combination comprising at least one of the foregoing solvents.

Coated Substrate

The underlayer coating composition disclosed herein may be used to form a film comprising the underlayer coating composition, wherein the film on the substrate constitutes a coated substrate. Such a coated substrate may include: (a) a substrate having one or more layers to be patterned on a surface thereof; (b) a layer of the underlayer coating composition disposed on a substrate; and (c) a layer of the photoresist composition disposed on the layer of the underlayer coating composition or disposed on one or more layer to be patterned. For example, patterning may be carried out using ultraviolet radiation at a wavelength of less than 248 nm, and in particular, at 193 nm, or by using the EUV. The patternable film thus may include the photoacid generator.

Method of Forming Electronic Device

A method of forming an electronic device may therefore include: (a) coating a substrate with a layer of the underlayer coating composition; (b) curing the underlayer coating composition to form an underlayer film; (c) applying a layer of a photoresist composition on the underlayer film to form a photoresist layer; (d) pattern-wise exposing the photoresist layer to radiation; and (e) developing the exposed photoresist layer to provide a resist relief image.

Substrates may be of any dimension and shape, and may, for example, be those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. For example, the surfaces of substrates herein include critical dimension layers to be patterned including, for example, one or more gate-level layers or other critical dimension layer on the substrates for semiconductor manufacture. Such substrates may, for example, include silicon, SOI, strained silicon, and other such substrate materials, formed as circular wafers having dimensions such as, for example, 200 mm, 300 mm, or larger in diameter, or other dimensions useful for wafer fabrication production.

The resist underlayer coating compositions, according to embodiment of the present invention, provide additional acid to interface by the newly designed polymer structure and photo-acid generator having high EUV absorption so that photo-speed, scum/footing profile of EUV photo-resist can be improved. By the same mechanism, nano-bridging defects, which are observed after all pattern transfer, may be reduced significantly compared to photo-resist on CVD hardmask stack.

Hereinafter, the present disclosure is illustrated in more detail with reference to examples. However, these examples are exemplary, and the present disclosure is not limited thereto.

EXAMPLES

Synthesis of Polymers

Polymer Example 1

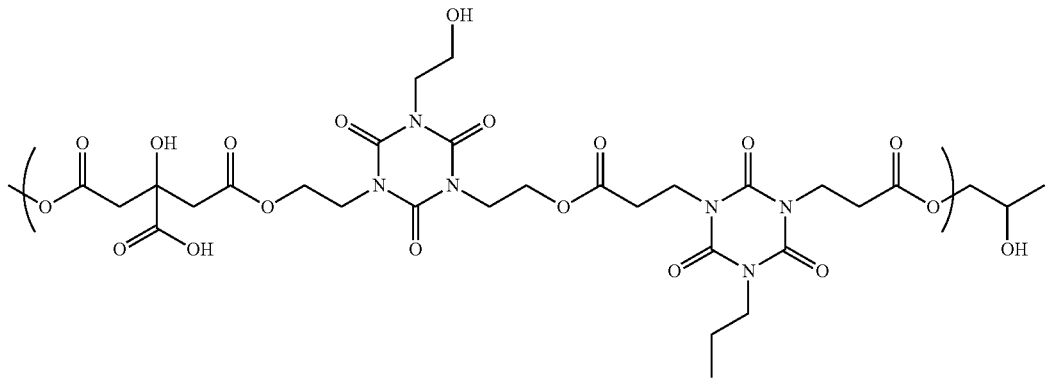

A 250 mL 3-neck round bottom flask was charged with tris(hydroxyethyl)isocyanurate (15.24 g), tris(carboxyethyl)isocyanurate (14.26 g), citric acid (11.21 g), 1,2-propane diol (5.33 g), propylene glycol monomethyl ether (10.0 g), anisole (50.0 g), and p-toluene sulfonic acid (0.44 g). The flask was connected to a condenser equipped with a Dean-Stark trap and a thermometer to measure and control the solution temperature throughout the polymerization. The flask was placed in a silicon oil bath equipped with a magnetic stirrer. The reactor temperature was set at 150° C. and maintained for 4 hours. After that time, the reactor was allowed to cool to room temperature while stirring. The polymer solution was precipitated into a ten-fold excess iso-propyl alcohol and the polymer was recovered by filtration and vacuum drying for 24 hours at 40° C. The dried powder was re-dissolved with tetrahydrofuran and then precipitated from a ten-fold excess iso-propyl alcohol. The white product was filtered and dried for 24 hours at 40° C. in a vacuum oven.

Polymer Example 2

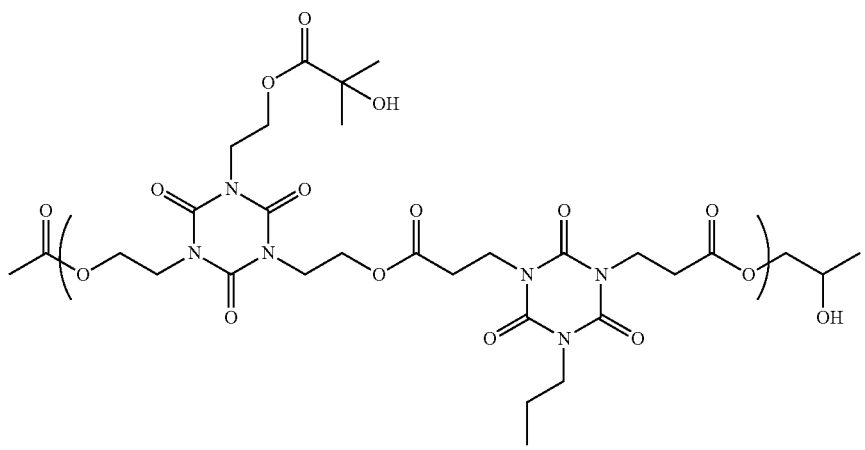

A 250 mL 3-neck round bottom flask was charged with tris(hydroxyethyl)isocyanurate (14.28 g), tris(carboxyethyl) isocyanurate (18.88 g), 1,2-propandiol (9.25 g), 2-hydroxyisobutyric acid (7.59 g), anisole (50.0 g), p-toluene sulfonic acid (0.58 g). The flask was connected to a condenser equipped with a Dean-Stark trap and a thermometer to measure and control the solution temperature throughout the polymerization. The flask was placed in a silicon oil bath equipped with a magnetic stirrer. The reactor temperature was set at 150° C. and maintained for 4 hours. After such time, the reactor was allowed to cool to room temperature while stirring. The polymer solution was precipitated into a ten-fold excess iso-propyl alcohol, and the polymer was recovered by filtration and vacuum drying for 24 hours at 40° C. The dried powder was re-dissolved with tetrahydrofuran and then precipitated from a ten-fold excess iso-propyl alcohol. The dried powder was re-dissolved with tetrahydrofuran and precipitated from a ten-fold excess iso-propyl alcohol. The white product was filtered and dried for 24 hours at 40° C. in a vacuum oven.

Polymer Example 3

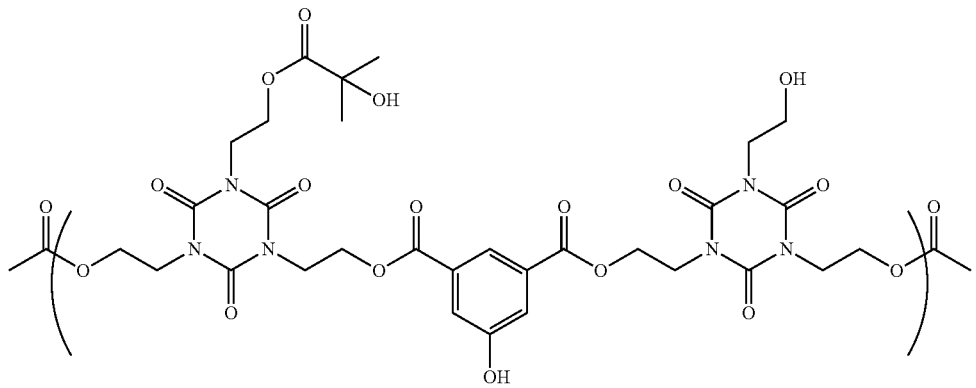

A 250 mL 3-neck round bottom flask was charged with tris(hydroxyethyl)isocyanurate (29.26 g), dimethyl-5-hydroxyisophtalate (10.10 g), 2-hydroxyisobutyric acid (10.00 g), anisole (44.61 g), p-toluene sulfonic acid (0.99 g). The flask was connected to a condenser equipped with a Dean-Stark trap and a thermometer to measure and control the solution temperature throughout the polymerization. The flask was placed in a silicon oil bath equipped with a magnetic stirrer. The reactor temperature was set at 150° C. and maintained for 8 hours. After such time, the reactor was allowed to cool to 40° C. while stirring. The resulting mixture was diluted by adding methyl 2-hydroxyisobutyrate (~20 weight %).

A 250 mL 3-neck round bottom flask was charged with a reaction mixture (131.80 g), tetramethoxymethylglycoluril (6.49 g), p-toluene sulfonic acid (prior to the reaction, the reaction mixture was analyzed for free p-toluene sulfonic acid content, then adjusted to 75 ppm based on the weight of solution). The flask was equipped with nitrogen inlet, water cooled condenser and a thermometer to measure and control the solution temperature throughout the polymerization. The flask was placed in a silicon oil bath equipped with a magnetic stirrer. The reactor temperature was set at 70° C. and maintained for 5 hours. After the end of reaction, the reactor was allowed to cool to room temperature while stirring. The polymer solution was precipitated into a ten-fold excess iso-propyl alcohol, and the polymer was recovered by filtration and vacuum drying for 24 hours at 50° C.

Polymer Example 4

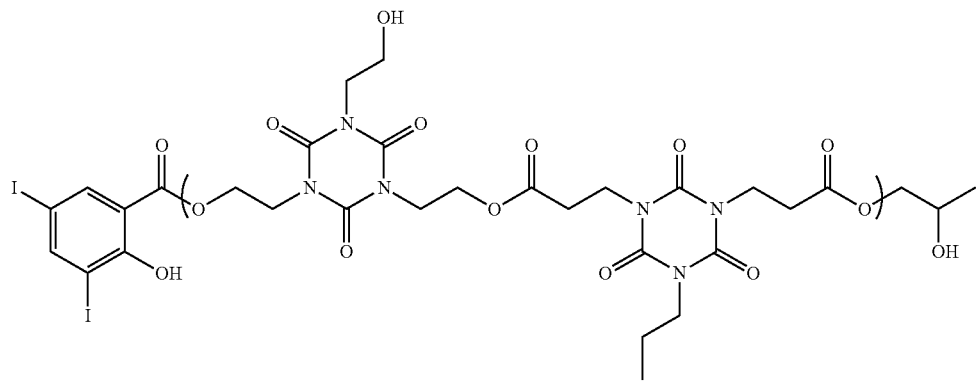

A 250 mL 3-neck round bottom flask was charged with tris(hydroxyethyl)isocyanurate (11.37 g), tris(carboxyethyl) isocyanurate (15.03 g), diiiodosalicylic acid (16.98 g), 1,2-propandiol (6.63 g), propyleneglycol monomethyl ether (10.0 g), anisole (50.0 g), and p-toluene sulfonic acid (0.41 g). The flask was connected to a condenser equipped with a Dean-Stark trap and a thermometer to measure and control the solution temperature throughout the polymerization. The flask was placed in a silicon oil bath equipped with a magnetic stirrer. The reactor temperature was set at 150° C. and maintained for 3 hours. After such time, the reactor was allowed to cool to room temperature while stirring. The polymer solution was precipitated into a ten-fold excess iso-propyl alcohol, and the polymer was recovered by filtration and vacuum drying for 24 hours at 40° C. The dried powder was re-dissolved with tetrahydrofuran and then precipitated from a ten-fold excess iso-propyl alcohol. The white product was filtered and dried for 24 hours at 40° C. in a vacuum oven.

Polymer Example 5

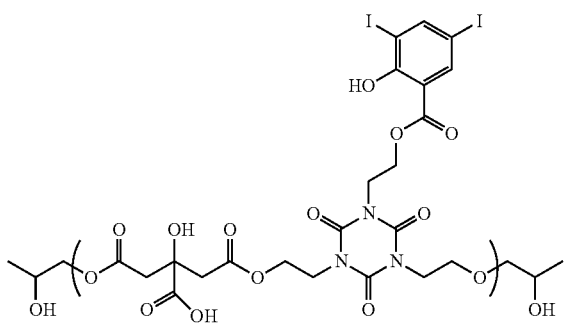

A 250 mL 3-neck round bottom flask was charged with tris(hydroxyethyl)isocyanurate (15.24 g), citric acid (11.21 g), diiodosalicylic acid (18.21 g), 1,2-propandiol (5.33 g), propyleneglycol monomethyl ether (10.0 g), anisole (50.0 g), p-toluene sulfonic acid (0.44 g). The flask was connected to a condenser equipped with a Dean-Stark trap and a thermometer to measure and control the solution temperature throughout the polymerization. The flask was placed in a silicon oil bath equipped with a magnetic stirrer. The reactor temperature was set at 150° C. and maintained for 3 hours. After such time, the reactor was allowed to cool to room temperature while stirring. The polymer solution was precipitated into a ten-fold excess iso-propyl alcohol, and the polymer was recovered by filtration and vacuum drying for 24 hours at 40° C. The dried powder was re-dissolved with tetrahydrofuran and then precipitated from a ten-fold excess iso-propyl alcohol. The dried powder was re-dissolved with tetrahydrofuran and then precipitated from a ten-fold excess iso-propyl alcohol. The white product was filtered and dried for 24 hours at 40° C. in a vacuum oven.

Polymer Example 6

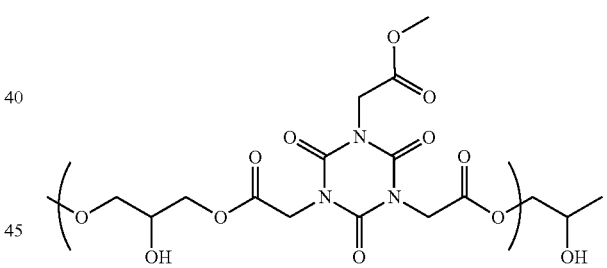

A 250 mL 3-neck round bottom flask was charged with glycerol (5.41 g), tris(carboxymethyl) isocyanurate (35.64 g), 1,2-propandiol (8.95 g), anisole (50.0 g), p-toluene sulfonic acid (0.56 g). The flaks was connected to a condenser equipped with a Dean-Stark trap and a thermometer to measure and control the solution temperature throughout the polymerization. The flask was placed in a silicon oil bath equipped with a magnetic stirrer. The reactor temperature was set at 150° C. and maintained for 2 hours. After such time, the reactor was allowed to cool to room temperature while stirring. The polymer solution was precipitated into a ten-fold excess iso-propyl alcohol, and the polymer was recovered by filtration and vacuum drying for 24 hours at 40° C. The dried powder was re-dissolved with tetrahydrofuran and then precipitated from a ten-fold excess iso-propyl alcohol. The dried powder was re-dissolved with tetrahydrofuran and then precipitated from a ten-fold excess iso-propyl alcohol. The white product was filtered and dried for 24 hours at 40° C. in a vacuum oven.

Comparative Polymer Example 1

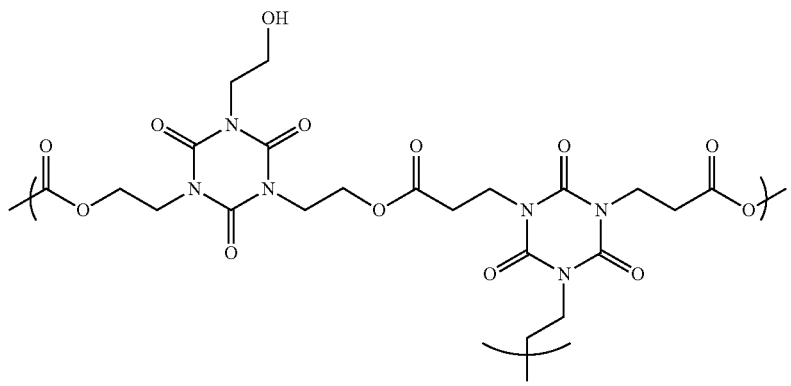

A 3-necked 100 mL round bottom flask was equipped with a thermocouple, Dean-Stark, a condenser and a heating oil bath. Tris(2-hydroxyethyl) iso-cyanurate (30.4 g), tris(2-carboxyethyl) iso-cyanurate (20.1 g, 58.2 mmol), n-butanol (20.0 g, 270.0 mmol), p-toulenesulfonic acid (0.5 g, 2.8 mmol), and 34 g of anisole were weighed into a flask. The reaction mixture was heated to 150° C. with stirring for 3 hours, cooled to room temperature, and the mixture solution was precipitated with iso-propyl alcohol/heptane, filtered, and vacuum dried for 24 hours at 40° C.

Preparation of Photoacid Generators (PAG)

PAG Synthesis Example 1

To a clean 100 mL round bottom flask equipped with a stir bar was added a solution of bis(4-tert-butylphenyl)iodonium chloride (1.000 g, 2.332 mmol) in dichloromethane (10 mL) and another solution of lithium nonafluoro-1-butane sulfate (1.142 g, 3.732 mmol) in H$_2$O (10 mL). The reaction mixture was stirred at room temperature overnight. The organic layer was separated and washed with 5 mL H$_2$O three times. The solvent was evaporated under reduced pressure and the resulting solid was dried in a vacuum oven. The product was obtained as white solid, 1.425 g (88%). $^1$H NMR (600 MHz, DMSO-d$_6$) δ (ppm)=8.16 (dt, 4H), 7.55 (dt, 4H), 1.26 (s, 18H). $^{19}$F NMR (564.686 MHz, DMSO-d$_6$) δ (ppm)=−80.42 (t, 3F), −114.82 (t, 2F), −121.37 (q, 2F), −125.66 (t, 2F).

PAG Synthesis Example 2

To a clean 100 mL round bottom flask equipped with a stir bar was added a solution of diphenyliodonium trifluoromethane sulfate (1.024 g, 2.380 mmol) in dichloromethane (10 mL) and another solution of lithium nonafluoro-1-butane sulfate (1.093 g, 3.571 mmol) in H$_2$O (10 mL). The reaction mixture was stirred at room temperature overnight. The organic layer was separated and washed with 5 mL H$_2$O three times. The solvent was evaporated under reduced pressure and the resulting solid was dried in a vacuum oven. The product was obtained as white solid, 1.100 g (80%). $^1$H NMR (600 MHz, DMSO-d$_6$) δ (ppm)=8.26-8.24 (m, 4H), 7.67 (tt, 2H), 7.54 (tt, 4H). $^{19}$F NMR (565 MHz, DMSO-d$_6$) δ (ppm)=−80.42 (t, 3F), −114.82 (t, 2F), −121.37 (q, 2F), −125.66 (t, 2F).

PAG Synthesis Example 3

To a clean 100 mL round bottom flask equipped with a stir bar was added a solution of bis(4-fluorophenyl)iodonium trifluoromethane sulfate (1.000 g, 2.145 mmol) in dichloromethane (10 mL) and another solution of lithium nonafluoro-1-butane sulfate (1.050 g, 3.432 mmol) in H$_2$O (10 mL). The reaction mixture was stirred at room temperature overnight. The organic layer was separated and washed with 5 mL H$_2$O three times. The solvent was evaporated under reduced pressure and the resulting solid was dried in a vacuum oven. The product was obtained as white solid, 1.144 g (87%). $^1$H NMR (600 MHz, DMSO-d$_6$) δ (ppm)= 8.35-8.32 (m, 4H), 7.45-7.41 (m, 4H). $^{19}$F NMR (565 MHz, DMSO-d$_6$) δ (ppm)=−80.41 (t, 3F), −106.63 (t, 2F), −114.82 (t, 2F), −121.37 (q, 2F), −125.66 (t, 2F).

PAG Synthesis Example 4

To a clean 1 L round bottom flask equipped with a stir bar was added a solution of bis(4-tert-butylphenyl)iodonium chloride (20.000 g, 46.644 mmol) in dichloromethane (250 mL) and another solution of Na-AdOHDFMS (25.350 g, 69.966 mmol) in H$_2$O (250 mL). The reaction mixture was stirred at room temperature overnight. The organic layer was separated and washed with 150 mL H$_2$O three times. The solvent was evaporated under reduced pressure and the resulting solid was dried in a vacuum oven. The product was obtained as white solid, 30.305 g (89%). $^1$H NMR (600 MHz, DMSO-d$_6$) δ (ppm)=8.15 (dt, 4H), 7.55 (dt, 4H), 4.42 (s, 1H), 3.86 (s, 2H), 2.09 (m, 2H), 1.53-1.36 (m, 12H), 1.27 (s, 18H).

PAG Synthesis Example 5

To a clean 250 mL round bottom flask equipped with stir bar was added a solution of bis(4-fluorophenyl)iodonium trifluoromethanesulfonate (3.19 g, 6.83 mmol) in dichloromethane (100 mL) and another solution of sodium 1,1-difluoro-2-(((1r,3s,5R,7S)-3-hydroxyadamantan-1-yl) methoxy)-2-oxoethane-1-sulfonate (2.338 g, 10.26 mmol) in deionized water. After stirring at room temperature for 16 hours, the H$_2$O layer was removed. The crude NMR spectrum of the intermediates was taken to check the reaction progress. More of the solution containing sodium 1,1-difluoro-2-(((1r,3s,5R,7S)-3-hydroxyadamantan-1-yl) methoxy)-2-oxoethane-1-sulfonate (1.6 g, 5.1 mmol) was added. After stirring at room temperature for 16 hours, 0.31 g of the sodium 1,1-difluoro-2-(((1r,3s,5R,7S)-3-hydroxy-adamantan-1-yl)methoxy)-2-oxoethane-1-sulfonate was added. The aqueous and organic phases were separated. The organic phase was washed with water (15 mL) three times, and the solvent was removed under reduced pressure. The product was obtained as a solid—3.9 g (86%). $^1$H NMR (600 MHz, DMSO-d6): δ (ppm) 8.32 (m, 4H), 7.42 (m, 4H), 4.43 (s, 1H), 3.86 (s, 2H), 2.09 (m, 2H), 1.53~1.38 (m, 12H). $^{19}$F NMR (564 MHz, DMSO-d6): δ (ppm) −106.66 (s, 2H), −109.00 (s, 2H).

PAG Synthesis Example 6

To a clean 100 mL round bottom flask equipped with stir bar was added a solution of diphenyliodonium trifluoromethanesulfonate (1 g, 2.34 mmol) in dichloromethane (30 ml) and another solution of sodium 1,1-difluoro-2-(((1 r,3 s,5R,7S)-3-hydroxyadamantan-1-yl)methoxy)-2-oxoethane-1-sulfonate (1.7 g, 4.69 mmol) in deionized water (15 mL). After stirring at room temperature for 16 hours, the $H_2O$ layer was removed. The crude NMR spectrum of the intermediates was taken to check the reaction progress. More of the solution containing sodium 1,1-difluoro-2-(((1R,3S,5R,7S)-3-hydroxyadamantan-1-yl)methoxy)-2-oxoethane-1-sulfonate (0.43 g, 1.17 mmol) was added. After stirring at room temperature for 16 hours, the aqueous and organic phases were separated. The organic phase was washed with water (7 mL) eight times, and the solvent was removed under reduced pressure. The product was obtained solid as a solid—0.8 g (55%). $^1$H NMR (600 MHz, DMSO-d6): δ (ppm) 8.24 (m, 4H), 7.67 (m, 2H), 7.54 (m, 4H), 4.42 (s, 1H), 3.86 (s, 2H), 2.09 (m, 2H), 1.55~1.38 (m, 12H). $^{19}$F NMR (564 MHz, DMSO-d6): δ (ppm) −109.00 (s, 2H).

Reduction Potential Measurement of PAG

The electrochemical experiment was performed using a BASi Epsilon potentiostat equipped with a platinum working electrode, platinum wire auxiliary electrode, and an Ag/AgCl reference electrode. All instrumentation (electrodes, analytical cell, and stir bar) are cleaned with acetone prior to every use. The electrolyte solution consisted of 0.1 M tetrabutylammonium hexafluorophosphate (TBAH) in anhydrous acetonitrile. After being purged, a baseline reading was taken prior to adding the 10-3 M analyte (in this case PAG) to the solution. The measurement was swept across an electrochemical potential window of 0 to −2.0 V vs Ag/AgCl. The scan rate for potential sweep was 0.1 V/s with a step size of 0.01 V. The results are summarized in Table 1.

TABLE 1

| PAG | Reduction Potential (V) |
|---|---|
| TPS-Nf (comparative example) | −1.27 |
| PAG 1 | −0.83 |
| PAG 2 | −0.69 |

Preparation of Underlayer Coating Compositions

Composition Example 1

0.24 g of the Polymer Example 1, 0.02 g of a tetra methoxy methyl glycoluril as a crosslinker, and 0.003 g of 2,4,6-trimethylpyridinium p-toluenesulfonate salt were dissolved in 27.9 g of methyl-2-hydroxy isobutyrate, 69.8 g of propylene glycol monomethyl ether acetate, and 2 g of gamma-butyrolactone solvent mixture to obtain the solution. Then, the solution was filtered through PTFE 0.45 micron membrane filter.

Composition Example 2

0.20 g of Polymer Example 2, 0.02 g of a tetra methoxy methyl glycoluril as a crosslinker, and 0.003 g of 2,4,6-trimethylpyridinium p-toluenesulfonate salt were dissolved in 27.9 g of methyl-2-hydroxy isobutyrate, 69.8 g of propylene glycol monomethyl ether acetate, and 2 g of gamma-butyrolactone solvent mixture to obtain the solution. Then, the solution was filtered through PTFE 0.45 micron membrane filter.

Composition Example 3

0.20 g of Polymer Example 3, 0.02 g of a tetra methoxy methyl glycoluril as a crosslinker, and 0.003 g of 2,4,6-trimethylpyridinium p-toluenesulfonate salt were dissolved in 27.9 g of methyl-2-hydroxy isobutyrate, 69.8 g of propylene glycol monomethyl ether acetate, and 2 g of gamma-butyrolactone solvent mixture to obtain the solution. Then, the solution was filtered through PTFE 0.45 micron membrane filter.

Composition Example 4

0.20 g of Polymer Example 3, 0.02 g of a tetra methoxy methyl glycoluril as a crosslinker, 0.003 g of 2,4,6-trimethylpyridinium p-toluenesulfonate salt, and 0.03 g of the PAG 1 were dissolved in 27.9 g of methyl-2-hydroxy isobutyrate, 69.8 g of propylene glycol monomethyl ether acetate, and 2 g of gamma-butyrolactone solvent mixture to obtain the solution. Then, the solution was filtered through PTFE 0.45 micron membrane filter.

Comparative Composition Example 1

0.15 g of Comparative Polymer Example 1, 0.01 g of a tetra methoxy methyl glycoluril as a crosslinker, and 0.002 g of 2,4,6-trimethylpyridinium p-toluenesulfonate salt were dissolved in 97.8 g of methyl-2-hydroxy isobutyrate, and 2 g of gamma-butyrolactone solvent mixture to obtain the solution. Then, the solution was filtered through PTFE 0.45 micron membrane filter.

Resist Pattern Formation Test

All prepared compositions were spin coated on a silicon wafer at 1,500 rpm using a spinner and the wafer was heated at 205° C. for 1 minute on a hot plate to form thin film for E-Beam lithography (film thickness of 5 nm). Onto the resist underlayer film for E-beam lithography, a resist solution (methacrylate based positive type chemically amplified e-beam resist) was applied with a spinner and heated on a hot plate to form a resist film (a film thickness of 40 nm). The dose of operation for 40 nm 1 to 1 L/S patterning resist on underlayer examples were evaluated direct e-beam writing by E-Beam lithography tools (JBX 9300FS from JEOL 100 keV).

TABLE 2

| Resist underlayer film-forming composition | $E_{op}$ for 40 nm half-pitch patterning (uC/cm$^2$) | Top view profile at $E_{op}$ |
|---|---|---|
| Example 1 | 260 | No scum and bridge |
| Example 2 | 260 | No scum and bridge |
| Example 3 | 260 | No scum and bridge |
| Example 4 | 240 | No scum and bridge |
| Comparative Example 1 | 520 | Scum and severe bridge |

Examples in this invention showed much faster $E_{op}$ than conventional underlayer (comparative example) proving additional acid generation concept by specific functional moieties of polymers and PAG in this invention. E-beam lithography was adopted as a test method because patterning mechanism of CAR in e-beam is same with EUV lithography. Top view profile also verified advantages of this invention. Working examples of this invention showed no scum and bridge while photoresist on comparative example exhibit severe bridge on L/S patterns.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. An underlayer coating composition, comprising:
a polymer comprising:
repeat units derived from a monomer represented by Chemical Formula (1):

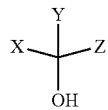

(1)

wherein,
X is a linear or branched C1 to C10 hydrocarbon group, a C1 to C10 alkoxycarbonyl group, a carboxylic acid group, or a linear or branched C1 to C10 hydroxyalkyl group optionally substituted with a C1 to C5 alkoxycarbonyl group or a C1 to C5 substituted alkoxy group;
Y is a hydrogen, a linear or branched C1 to C10 hydrocarbon group, a C1 to C10 alkoxycarbonyl group, a carboxylic acid group, or a linear or branched C1 to C10 hydroxyalkyl group optionally substituted with a C1 to C5 alkoxycarbonyl group or a C1 to C5 alkoxy group; and
Z is a linear or branched C1 to C10 hydrocarbon group, a C1 to C10 alkoxycarbonyl group, a carboxylic acid group, or a linear or branched C1 to C10 hydroxyalkyl group optionally substituted with a C1 to C5 alkoxycarbonyl group or a C1 to C5 alkoxy group,
wherein each of the C1 to C10 hydrocarbon group, the C1 to C10 alkoxycarbonyl group, and the C1 to C10 hydroxyalkyl group is optionally substituted with at least one selected from the group consisting of fluorine, chlorine, bromine, iodine, a hydroxyl group, a thiol group, a carboxylic acid group, a C1 to C5 alkyl group, a C3 to C8 cycloalkyl group, a C2 to C5 alkenyl group, a C1 to C5 alkoxy group, a C2 to C5 alkenoxy group, a C6 to C10 aryl group, a C6 to C10 aryloxy group, a C7 to C10 alkylaryl group, and a C7 to C10 alkylaryloxy group,
provided that at least one selected from X, Y, and Z is:
a linear or branched C1 to C10 hydrocarbon group substituted with at least one selected from the group consisting of a hydroxyl group, a thiol group, a carboxylic acid group, a C2 to C5 alkenyl group, a C1 to C5 alkoxy group, a C2 to C5 alkenoxy group, a C6 to C10 aryloxy group, and a C7 to C10 alkylaryloxy group,
a C1 to C10 alkoxycarbonyl group,
a carboxylic acid group, or
a linear or branched C1 to C10 hydroxyalkyl group optionally substituted with a C1 to C5 alkoxycarbonyl group or a C1 to C5 alkoxy group, and
repeat units derived from a monomer represented by Chemical Formula (3):

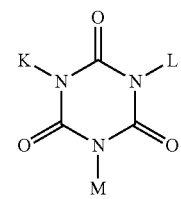

(3)

wherein,
K, L, and M are each independently a linear or branched C1 to C10 hydrocarbon group, a C1 to C10 alkoxycarbonyl group, a C1 to C10 alkanoyloxy group, each of which is optionally substituted with a carboxylic acid group, or a linear or branched C1 to C10 hydroxyalkyl group optionally substituted with a C1 to C5 alkoxycarbonyl group or a C1 to C5 substituted alkoxy group,
wherein each of the C1 to C10 hydrocarbon group, the C1 to C10 alkoxycarbonyl group, the C1 to C10 alkanoyloxy group, and the C1 to C10 hydroxyalkyl group is optionally substituted with at least one selected from the group consisting of fluorine, chlorine, bromine, iodine, C1 to C5 alkyl, C3 to C8 cycloalkyl, C2 to C5 alkenyl, C1 to C5 alkoxy, C2 to C5 alkenoxy, C6 to C10 aryl, C6 to C10 aryloxy, C7 to C10 alkylaryl, and C7 to C10 alkylaryloxy, and
4 to 15 wt % of a photoacid generator comprising an iodonium cation, based on total solid content of the underlayer coating composition.

2. The underlayer coating composition of claim 1, further comprising repeat units derived from a monomer represented by Chemical Formula (2):

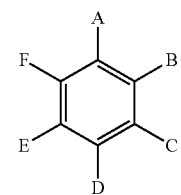

(2)

wherein,
A, B, C, D, E, and F are each independently a hydrogen, a halogen, a hydroxyl group, a carboxylic acid group, a C1 to C10 alkoxycarbonyl group, a C1 to C10 alkoxy group, a linear or branched C1 to C10 hydrocarbon group, or a C1 to C10 alkanoyloxy group,
wherein each of the C1 to C10 alkoxycarbonyl group, the C1 to C10 alkoxy group, the C1 to C10 hydrocarbon group, and the C1 to C10 alkanoyloxy group is optionally substituted with at least one selected from the group consisting of fluorine, chlorine, bromine, iodine, C1 to C5 alkyl, C3 to C8 cycloalkyl, C2 to C5 alkenyl, C1 to C5 alkoxy, C2 to C5 alkenoxy, C6 to C10 aryl, C6 to C10 aryloxy, C7 to C10 alkylaryl, and C7 to C10 alkylaryloxy, and wherein at least two selected from A, B, C, D, E, and F are independently selected from the group consisting of:
- a linear or branched C1 to C10 hydrocarbon group substituted with at least one selected from the group consisting of a hydroxyl group, a carboxylic acid group, a C2 to C5 alkenyl group, a C1 to C5 alkoxy group, a C2 to C5 alkenoxy group, a C6 to C10 aryloxy group, and a C7 to C10 alkylaryloxy group,
- a C1 to C10 alkoxy group,
- a C1 to C10 alkoxycarbonyl group,
- a C1 to C10 alkanoyloxy group,
- a carboxylic acid group, or
- a hydroxyl group.

3. The underlayer coating composition of claim 1, wherein in Chemical Formula (1), at least one selected from X, Y, and Z comprises a carboxylic acid group.

4. The underlayer coating composition of claim 2, wherein in Chemical Formula (2), at least one selected from A, B, C, D, E, and F comprises an iodine.

5. The underlayer coating composition of claim 1, wherein in Chemical Formula (3), at least one selected from K, L, and M comprises a hydroxyalkyl group.

6. The underlayer coating composition of claim 1, further comprising:
   a crosslinking agent; and
   a solvent.

7. A coated substrate comprising:
   a layer of the underlayer coating composition of claim 1 disposed on a substrate, and
   a photoresist layer disposed on the layer of the underlayer coating composition.

8. A method of forming an electronic device, comprising:
   (a) applying a layer of the underlayer coating composition of claim 1 on a substrate;
   (b) curing the underlayer coating composition to form an underlayer film;
   (c) applying a layer of a photoresist composition on the underlayer film to form a photoresist layer;
   (d) pattern-wise exposing the photoresist layer to radiation; and
   (e) developing the exposed photoresist layer to provide a resist relief image.

9. The underlayer coating composition of claim 1, wherein the photoacid generator is selected from:

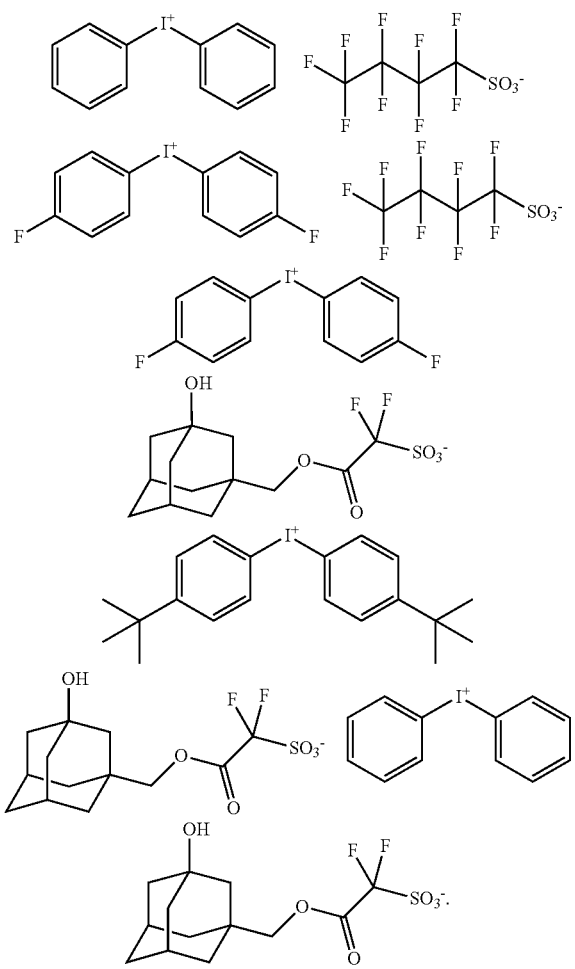

10. The underlayer coating composition of claim 1, wherein the monomer represented by Chemical Formula (1) does not comprise an aromatic ring group, a heteroaromatic ring group, or an epoxy group.

11. The underlayer coating composition of claim 1, wherein Y is not hydrogen.

\* \* \* \* \*